United States Patent
Hildt et al.

(10) Patent No.: US 7,018,826 B1
(45) Date of Patent: Mar. 28, 2006

(54) PARTICLES FOR GENE THERAPY

(75) Inventors: Eberhard Hildt, Berlin (DE); Peter Hofschneider, Munich (DE)

(73) Assignee: Island Pharmaceuticals Ltd., Douglas (GB)

( * ) Notice: Subject to any disclaimer, the term of this patent is extended or adjusted under 35 U.S.C. 154(b) by 0 days.

(21) Appl. No.: 09/890,752

(22) PCT Filed: Feb. 4, 2000

(86) PCT No.: PCT/DE00/00363

§ 371 (c)(1),
(2), (4) Date: Nov. 30, 2001

(87) PCT Pub. No.: WO00/46376

PCT Pub. Date: Aug. 10, 2000

(30) Foreign Application Priority Data

Feb. 5, 1999 (DE) ................................ 199 04 800

(51) Int. Cl.
*C12N 7/00* (2006.01)

(52) U.S. Cl. .................. 435/235.1; 435/69.1; 435/455; 435/456; 435/173.3; 435/320.1; 530/300; 530/350

(58) Field of Classification Search ............... 435/69.1, 435/455, 456, 173.3, 235.1, 320.1; 530/300, 530/350
See application file for complete search history.

(56) References Cited

FOREIGN PATENT DOCUMENTS

| WO | WO 93/20221 | | 10/1993 |
|---|---|---|---|
| WO | WO 97/24453 | * | 7/1997 |
| WO | WO 00/26379 | | 5/2000 |

OTHER PUBLICATIONS

Schodel Journal of Biotechnology 1996 vol. 44, pp. 91-96.*
Dmitriev, I. et al., "*An Adenovirus Vector with Genetically Modified Fibers Demonstrates Expanded Tropism via Utilization of a Coxsackievirus and Adenovirus Receptor-Independent Cell Entry Mechanism*", Journal of Virology, pp. 9706-9713, Dec. (1998).
Oess, S. et al., "*Novel Cell Permeable Motif Derived from the PreS2-domain of Hepatitis-B Virus Surface Antigens*", Gene Therapy,9 pages, May (2000).
Schodel, F et al., "*Hybrid Hepatitis B Virus Core Antigen as a Vaccine Carrier Moiety: I. Presentation of Foreign Epitopes*", Journal of Biotechnology, pp. 91-96, Jan. (1996).
Derossi, D. et al., "The Third Helix of the Antennapedia Homeodomain translocates through Biological Membranes." J. Biol. Chem. 1994. 269(14): pp. 10444-10450.
Vives, E. et al., "A Truncated HIV-1 Tat Protein Basic Domain Rapidly Translocates through the Plasma Membrane and Accumulates in the Cell Nucleus." J. Biol. Chem. 1997. 272(25): pp. 16010-16017.
Rojas, M. et al., "Genetic Engineering of Proteins with Cell Membrane Permeability." Nat. Biotechnol. 1998. 16(4): pp. 370-375.
Elliot g., et al., "Intercellular Trafficking and Protein Delivery by a Herpesvirus Structural Protein." Cell, 1997. 88(2): pp. 223-233.
Phelan, A. et al, "Intercellular Delivery of Functional p53 by the Herpesvirus Protein VP22."Nat. Biotechnol. 1998. 16 (5): pp. 440-443.

* cited by examiner

*Primary Examiner*—James Housel
*Assistant Examiner*—Myron G. Hill
(74) *Attorney, Agent, or Firm*—Wilmer Cutler Pickering Hale and Dorr LLP

(57) ABSTRACT

The present invention relates to particles, comprising: a protein envelope with a fusion protein, which comprises a virus protein, a cell permeability-mediating peptide and a heterologous cell-specific binding site; and a nucleic acid present in the protein envelope, which comprises the sequence for a virus-specific packaging signal and a structural gene. The invention further relates to methods for the preparation of such particles and means suitable for this purpose, as well as the use of the particles in gene therapy.

10 Claims, 2 Drawing Sheets atgggccgtggcgaaggagctggagcattcgggctgggtttcaccccaccgcacggaggccttttggggtggagccctcaggctca
gggcatactacaaactttgccagcaaatccgcctcctgcctccaccaatcgccagacaggaaggcagcctaccccgctgtctccacct
ttgagaaacactcatcctcaggccatgcagtggaattccacaacctttcaccaaactctgcaagatcccagagtgagaggcctgtatttc
cctgctggtggctccagttcaggagcagtaaaccctgttccgactactgcctctcccttatcgtcaatcttctcgaggattggggaccctg
cgctgaacatggagaacatcacatcaggattcctaggacccctttctcgtgttacaggcggggttttcttgttgacaagaatcctcacaat
accgcagagtctagactcgtggtggacttctctcaattttctaggggggaactaccgtgtgtcttggccaaaattcgcagtccccaacctcc
aatcactcaccaacctcctgtcctccaacttgtcctggttatcgctggatgtgtctgcggcgttttatcatcttcctcttcatcctgctgctatg
cctcatcttcttgttggttcttctggactatcaaggtatgttgcccgtttgtcctctaattccaggatcctcaaccaccagcacgggaccatg
ccgaacctgcatgactactgctcaaggaacctctatgtatccctcctgttgctgtaccaaaccttcggacggaaattgcacctgtattccc
atcccatcatcctgggctttcggaaaattcctatgggagtgggcctcagcccgtttctcctggctcagtttactagtgccatttgttcagtgg
ttcgtagggctttccccccactgtttggctttcagttatatggatgatgtggtattgggggccaagtctgtacagcatcttgagtccctttttac
cgctgttaccaattttcttttgtctttgggtatacatttaaacc (SEQ ID NO: 4)

MGRGDGAGAFGLGFTPPHGGLLGWSPQAQGILETLPANPPPASTNRQSGRQPTPLSP
PLRNTHPQAMQWNSTTFHQTLQDPRVRGLYFPAGGSSSGTVNPVPTTVSPISSIFSRIG
DPALNMENITSGFLGPLLVLQAGFFLLTRILTIPQSLDSWWTSLNFLGGTTVCLGQNS
QSPTSNHSPTSCPPTCPGYRWMCLRRFIIFLFILLLCLIFLLVLLDYQGMLPVCPLIPGSS
TTSTGPCRTCTTPAQGTSMYPSCCCTKPSDGNCTCIPIPSSWAFGKFLWEWASARFS
WLSLLVPFVQWFVGLSPTVWLSVIWMMWYWGPSLYSILSPFLPLLPIFFCLWVYI
(SEQ. ID NO: 1)

FIG. 1 atgcccatatcgtcaatcttctcgaggattggggaccctggatccactactgttcaagcctccaagctgtgccttgggtggctttggggc
atggacatcgacccttataaagaatttggagctactgtggagttactctcgttttttgccttctgacttctttccttcagtacgagatcttctaga
taccgcctcagctctgtatcgggaagccttagagtctcctgagcattgttcacctcaccatactgcactcaggcaagcaattctttgctgg
ggggaactaatgactctagctacctgggtgggtgttaatttggaagatccagaattccgaggcgacgcgtctagagacctagtagtcag
ttatgtcaacactaatatgggcctaaagttcaggcaactcttgtggtttcacatttcttgtctcacttttggaagagaaaccgttatagagtatt
tggtgtctttcggagtgtggattcgcactcctccagcttatagaccaccaaatgcccctatcctatcaacacttccggaaactactgttgtta
gacgacgaggcaggtcccctagaagaagaactccctcgcctcgcagacgaaggtctcaatcgccgcgtcgcagaagatctcaatct
cgggaacctcaatgttagtattcc (SEQ ID NO: 3)

MPLSSIFSRIGDPTVQASKLCLGWLWGMDIDPYKEFGATVELLSFLPSDFFPSVRDLL
DTASALYREALESPEHCSPHHTALRQAILCWGELMTLATWVGVNLEDPEF<u>RGD</u>ASR
DLVVSYVNTNMGLKFRQLLWFHISCLTFGRETVIEYLVSFGVWIRTPPAYRPPNAPIL
STLPETTVVRRRGRSPRRRTPSPRRRRSQSPRRRRSQSREPQC (SEQ ID NO: 2)

FIG. 2

SEQUENCE LISTING

```
<160> NUMBER OF SEQ ID NOS: 21

<210> SEQ ID NO 1
<211> LENGTH: 347
<212> TYPE: PRT
<213> ORGANISM: Artificial Sequence
<220> FEATURE:
<223> OTHER INFORMATION: Fusion protein comprising a LHBs and
      heterologous binding site RGD

<400> SEQUENCE: 1

Met Gly Arg Gly Asp Gly Ala Gly Ala Phe Gly Leu Gly Phe Thr Pro
1               5                   10                  15

Pro His Gly Gly Leu Leu Gly Trp Ser Pro Gln Ala Gln Gly Ile Leu
            20                  25                  30

Glu Thr Leu Pro Ala Asn Pro Pro Ala Ser Thr Asn Arg Gln Ser
        35                  40                  45

Gly Arg Gln Pro Thr Pro Leu Ser Pro Pro Leu Arg Asn Thr His Pro
    50                  55                  60

Gln Ala Met Gln Trp Asn Ser Thr Thr Phe His Gln Thr Leu Gln Asp
65                  70                  75                  80

Pro Arg Val Arg Gly Leu Tyr Phe Pro Ala Gly Gly Ser Ser Ser Gly
                85                  90                  95

Thr Val Asn Pro Val Pro Thr Thr Val Ser Pro Ile Ser Ser Ile Phe
            100                 105                 110

Ser Arg Ile Gly Asp Pro Ala Leu Asn Met Glu Asn Ile Thr Ser Gly
```

-continued

```
            115                 120                 125
Phe Leu Gly Pro Leu Leu Val Leu Gln Ala Gly Phe Phe Leu Leu Thr
        130                 135                 140

Arg Ile Leu Thr Ile Pro Gln Ser Leu Asp Ser Trp Trp Thr Ser Leu
145                 150                 155                 160

Asn Phe Leu Gly Gly Thr Thr Val Cys Leu Gly Gln Asn Ser Gln Ser
                165                 170                 175

Pro Thr Ser Asn His Ser Pro Thr Ser Cys Pro Pro Thr Cys Pro Gly
            180                 185                 190

Tyr Arg Trp Met Cys Leu Arg Arg Phe Ile Ile Phe Leu Phe Ile Leu
                195                 200                 205

Leu Leu Cys Leu Ile Phe Leu Leu Val Leu Leu Asp Tyr Gln Gly Met
        210                 215                 220

Leu Pro Val Cys Pro Leu Ile Pro Gly Ser Ser Thr Thr Ser Thr Gly
225                 230                 235                 240

Pro Cys Arg Thr Cys Thr Thr Pro Ala Gln Gly Thr Ser Met Tyr Pro
                245                 250                 255

Ser Cys Cys Cys Thr Lys Pro Ser Asp Gly Asn Cys Thr Cys Ile Pro
            260                 265                 270

Ile Pro Ser Ser Trp Ala Phe Gly Lys Phe Leu Trp Glu Trp Ala Ser
                275                 280                 285

Ala Arg Phe Ser Trp Leu Ser Leu Leu Val Pro Phe Val Gln Trp Phe
        290                 295                 300

Val Gly Leu Ser Pro Thr Val Trp Leu Ser Val Ile Trp Met Met Trp
305                 310                 315                 320

Tyr Trp Gly Pro Ser Leu Tyr Ser Ile Leu Ser Pro Phe Leu Pro Leu
                325                 330                 335

Leu Pro Ile Phe Phe Cys Leu Trp Val Tyr Ile
            340                 345

<210> SEQ ID NO 2
<211> LENGTH: 215
<212> TYPE: PRT
<213> ORGANISM: Artificial Sequence
<220> FEATURE:
<223> OTHER INFORMATION: Fusion protein comprising a HBcAg, a
      cell-permeability-mediating polypeptide and heterologous binding
      site RGD

<400> SEQUENCE: 2

Met Pro Leu Ser Ser Ile Phe Ser Arg Ile Gly Asp Pro Thr Val Gln
1               5                   10                  15

Ala Ser Lys Leu Cys Leu Gly Trp Leu Trp Gly Met Asp Ile Asp Pro
            20                  25                  30

Tyr Lys Glu Phe Gly Ala Thr Val Glu Leu Leu Ser Phe Leu Pro Ser
        35                  40                  45

Asp Phe Phe Pro Ser Val Arg Asp Leu Leu Asp Thr Ala Ser Ala Leu
    50                  55                  60

Tyr Arg Glu Ala Leu Glu Ser Pro Glu His Cys Ser Pro His His Thr
65                  70                  75                  80

Ala Leu Arg Gln Ala Ile Leu Cys Trp Gly Glu Leu Met Thr Leu Ala
                85                  90                  95

Thr Trp Val Gly Val Asn Leu Glu Asp Pro Glu Phe Arg Gly Asp Ala
            100                 105                 110

Ser Arg Asp Leu Val Val Ser Tyr Val Asn Thr Asn Met Gly Leu Lys
        115                 120                 125
```

-continued

```
Phe Arg Gln Leu Leu Trp Phe His Ile Ser Cys Leu Thr Phe Gly Arg
    130                 135                 140

Glu Thr Val Ile Glu Tyr Leu Val Ser Phe Gly Val Trp Ile Arg Thr
145                 150                 155                 160

Pro Pro Ala Tyr Arg Pro Pro Asn Ala Pro Ile Leu Ser Thr Leu Pro
                165                 170                 175

Glu Thr Thr Val Val Arg Arg Arg Gly Arg Ser Pro Arg Arg Arg Thr
            180                 185                 190

Pro Ser Pro Arg Arg Arg Arg Ser Gln Ser Pro Arg Arg Arg Ser
        195                 200                 205

Gln Ser Arg Glu Pro Gln Cys
    210                 215
```

<210> SEQ ID NO 3
<211> LENGTH: 663
<212> TYPE: DNA
<213> ORGANISM: Artificial Sequence
<220> FEATURE:
<223> OTHER INFORMATION: DNA coding for a fusion protein comprising a HBcAg, a cell-permeability-mediating polypeptide and heterologous binding site RGD

<400> SEQUENCE: 3

```
atgcccatat cgtcaatctt ctcgaggatt ggggaccctg gatccactac tgttcaagcc     60
tccaagctgt gccttgggtg gctttggggc atggacatcg acccttataa agaatttgga    120
gctactgtgg agttactctc gtttttgcct tctgacttct ttccttcagt acgagatctt    180
ctagataccg cctcagctct gtatcgggaa gccttagagt ctcctgagca ttgttcacct    240
caccatactg cactcaggca agcaattctt tgctgggggg aactaatgac tctagctacc    300
tgggtgggtg ttaatttgga agatccagaa ttccgaggcg acgcgtctag agacctagta    360
gtcagttatg tcaacactaa tatgggccta aagttcaggc aactcttgtg gtttcacatt    420
tcttgtctca cttttggaag agaaaccgtt atagagtatt tggtgtcttt cggagtgtgg    480
attcgcactc ctccagctta tagaccacca aatgccccta tcctatcaac acttccggaa    540
actactgttg ttagacgacg aggcaggtcc cctagaagaa gaactccctc gcctcgcaga    600
cgaaggtctc aatcgccgcg tcgcagaaga tctcaatctc gggaacctca atgttagtat    660
tcc                                                                   663
```

<210> SEQ ID NO 4
<211> LENGTH: 1047
<212> TYPE: DNA
<213> ORGANISM: Artificial Sequence
<220> FEATURE:
<223> OTHER INFORMATION: DNA coding for a fusion protein comprising a LHBs and heterologous binding site RGD

<400> SEQUENCE: 4

```
atgggccgtg gcgaaggagc tggagcattc gggctgggtt tcaccccacc gcacggaggc     60
cttttggggt ggagccctca ggctcagggc atactacaaa ctttgccagc aaatccgcct    120
cctgcctcca ccaatcgcca gacaggaagg cagcctaccc cgctgtctcc acctttgaga    180
aacactcatc ctcaggccat gcagtggaat tccacaacct ttcaccaaac tctgcaagat    240
cccagagtga gaggcctgta tttccctgct ggtggctcca gttcaggagc agtaaaccct    300
gttccgacta ctgcctctcc cttatcgtca atcttctcga ggattgggga ccctgcgctg    360
aacatggaga acatcacatc aggattccta ggaccccttc tcgtgttaca ggcggggttt    420
```

-continued

```
ttcttgttga caagaatcct cacaataccg cagagtctag actcgtggtg gacttctctc    480
aattttctag ggggaactac cgtgtgtctt ggccaaaatt cgcagtcccc aacctccaat    540
cactcaccaa cctcctgtcc tccaacttgt cctggttatc gctggatgtg tctgcggcgt    600
tttatcatct tcctcttcat cctgctgcta tgcctcatct tcttgttggt tcttctggac    660
tatcaaggta tgttgcccgt ttgtcctcta attccaggat cctcaaccac cagcacggga    720
ccatgccgaa cctgcatgac tactgctcaa ggaacctcta tgtatccctc ctgttgctgt    780 accaaaacctt cggacggaaa ttgcacctgt attcccatcc catcatcctg ggctttcgga   840
aaattcctat gggagtgggc ctcagcccgt ttctcctggc tcagtttact agtgccattt    900
gttcagtggt tcgtagggct ttcccccact gtttggcttt cagttatatg gatgatgtgg    960 tattggggc caagtctgta cagcatcttg agtccctttt taccgctgtt accaatttc     1020 ttttgtcttt gggtatacat ttaaacc                                         1047
```

<210> SEQ ID NO 5
<211> LENGTH: 35
<212> TYPE: DNA
<213> ORGANISM: Artificial Sequence
<220> FEATURE:
<223> OTHER INFORMATION: Primer

<400> SEQUENCE: 5
ccatattctt gggaacaaga tatccagcac ggggc                                 35

<210> SEQ ID NO 6
<211> LENGTH: 33
<212> TYPE: DNA
<213> ORGANISM: Artificial Sequence
<220> FEATURE:
<223> OTHER INFORMATION: Primer

<400> SEQUENCE: 6
ggattgctgg tggaagatat ctgccccgtg ctg                                   33

<210> SEQ ID NO 7
<211> LENGTH: 33
<212> TYPE: DNA
<213> ORGANISM: Artificial Sequence
<220> FEATURE:
<223> OTHER INFORMATION: Primer

<400> SEQUENCE: 7
cagcacgggg cagatatctt ccaccagcaa tcc                                   33

<210> SEQ ID NO 8
<211> LENGTH: 38
<212> TYPE: DNA
<213> ORGANISM: Artificial Sequence
<220> FEATURE:
<223> OTHER INFORMATION: Primer

<400> SEQUENCE: 8
gccccgtgct ggatatcatc ttgttcccaa gaatatgg                              38

<210> SEQ ID NO 9
<211> LENGTH: 36
<212> TYPE: DNA
<213> ORGANISM: Artificial Sequence
<220> FEATURE:
<223> OTHER INFORMATION: Primer

<400> SEQUENCE: 9
aaaagatctg gccgtggcga aggagctgga gcattc                             36

<210> SEQ ID NO 10
<211> LENGTH: 30
<212> TYPE: DNA
<213> ORGANISM: Artificial Sequence
<220> FEATURE:
<223> OTHER INFORMATION: Primer

<400> SEQUENCE: 10
aaaagatctg gtttaaatgt atacccaaag                                    30

<210> SEQ ID NO 11
<211> LENGTH: 33
<212> TYPE: DNA
<213> ORGANISM: Artificial Sequence
<220> FEATURE:
<223> OTHER INFORMATION: Primer

<400> SEQUENCE: 11
cccgatatca tgtcatctct tgttcatgtc cta                                33

<210> SEQ ID NO 12
<211> LENGTH: 30
<212> TYPE: DNA
<213> ORGANISM: Artificial Sequence
<220> FEATURE:
<223> OTHER INFORMATION: Primer

<400> SEQUENCE: 12
ggggatatcg gtcgatgtcc atgccccaaa                                    30

<210> SEQ ID NO 13
<211> LENGTH: 36
<212> TYPE: DNA
<213> ORGANISM: Artificial Sequence
<220> FEATURE:
<223> OTHER INFORMATION: Primer

<400> SEQUENCE: 13
gggggatccc gatgtacggg ccagatatac gcgttg                             36

<210> SEQ ID NO 14
<211> LENGTH: 27
<212> TYPE: DNA
<213> ORGANISM: Artificial Sequence
<220> FEATURE:
<223> OTHER INFORMATION: Primer

<400> SEQUENCE: 14
gggggatccg cggccgcttt acttgta                                       27

<210> SEQ ID NO 15
<211> LENGTH: 57
<212> TYPE: DNA
<213> ORGANISM: Artificial Sequence
<220> FEATURE:
<223> OTHER INFORMATION: DNA coding for a cell-permeability mediating
      peptide
<220> FEATURE:
<221> NAME/KEY: misc_feature
<222> LOCATION: (1)..(57)
<223> OTHER INFORMATION: Nucleotides 1-3 and 55-57 are "n" wherein
      "n" = any nucleotide.

<400> SEQUENCE: 15
nnnagatcta tgcccatatc gtcaatcttc tcgaggattg gggaccctgg atccnnn        57

<210> SEQ ID NO 16
<211> LENGTH: 30
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (1)..(3)
<223> OTHER INFORMATION: Nucleotides 1-3 "n" wherein "n" = any
      nucleotide.

<400> SEQUENCE: 16
nnnggatcca ctgttcaagc ctccaagctg        30

<210> SEQ ID NO 17
<211> LENGTH: 36
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (1)..(3)
<223> OTHER INFORMATION: Nucleotides 1-3 "n" wherein "n" = any
      nucleotide.

<400> SEQUENCE: 17
nnngaattct ggatcttcca aattaacacc caccca        36

<210> SEQ ID NO 18
<211> LENGTH: 39
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (1)..(3)
<223> OTHER INFORMATION: Nucleotides 1-3 "n" wherein "n" = any
      nucleotide.

<400> SEQUENCE: 18
nnngaattcc gaggcgacgc gtctagagac ctagtagtc        39

<210> SEQ ID NO 19
<211> LENGTH: 30
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (1)..(3)
<223> OTHER INFORMATION: Nucleotides 1-3 "n" wherein "n" = any
      nucleotide.

<400> SEQUENCE: 19
nnnaagcttt ccccaccttta tgagtccaag        30

<210> SEQ ID NO 20
<211> LENGTH: 12
<212> TYPE: PRT
<213> ORGANISM: Artificial Sequence
<220> FEATURE:
<223> OTHER INFORMATION: cell permeability-mediating peptide -continued

```
<400> SEQUENCE: 20

Pro Leu Ser Ser Ile Phe Ser Arg Ile Gly Asp Pro
1               5                   10

<210> SEQ ID NO 21
<211> LENGTH: 36
<212> TYPE: DNA
<213> ORGANISM: Artificial Sequence
<220> FEATURE:
<223> OTHER INFORMATION: DNA encoding cell permeability-mediating
      peptide

<400> SEQUENCE: 21
cccatatcgt caatcttctc gaggattggg gaccct                              36
```

PARTICLES FOR GENE THERAPY

This application is a national stage entry of PCT/DE00/00363, filed Feb. 4, 2000 which claims priority to GERMANY 199 04 800.2, filed Feb. 5, 1999.

BACKGROUND OF THE INVENTION

The present invention relates to nucleic acid containing particles which specifically bind to cells and can introduce their nucleic acid into these cells. The invention further relates to methods of preparing such particles and means suitable for this purpose as well as the use of the particles in gene therapy.

For gene therapy it is important to have a gene transfer system which is specific, in other words with which desired cells can be reached and genes can be introduced into these cells. In the case of liver cells, this is generally possible with a modified hepatitis B virus (HBV) as a vector, since HBV is specific for liver cells. For other cells, for example fibroblasts, there however exists no gene transfer system which yields satisfactory results.

It is therefore the object of the invention to provide a gene transfer system which is specific, in other words with which desired cells can be reached and genes can be introduced into these cells.

According to the invention, this is achieved by the subject matter in the claims.

SUMMARY OF THE INVENTION

The present invention is based on the recognition that nucleic acid-containing particles comprising a fusion protein which includes a virus protein, a cell permeability-mediating peptide, in particular such a peptide as described in the German patent application 198 50 718.6, and a heterologous cell-specific binding site, can bind to corresponding cells and can introduce their nucleic acid into these cells. For example, nucleic acid-containing HBV particles have been made which bind to fibroblasts and introduce their nucleic acid into these fibroblasts. To this end the hepatocyte binding site which is present in the region PreS1, in particular between amino acids 21–47, of the large surface protein of HBV (LHBs) was exchanged with the α5β1-integrin binding site of fibronectin, wherein the cell permeability-mediating peptide present in the region PreS2 of LHBs remained intact. Furthermore, particles have been made with specificity for fibroblasts by joining the core protein of HBV (HBcAg) with the α5β1-integrin binding site of fibronectin and the cell permeability-mediating peptide mentioned above. Moreover, the nucleic acid contained in the particles is expressed in the cells.

These findings were used to provide particles including: (a) a protein envelope with a fusion protein comprising a virus protein, a cell permeability-mediating peptide and a heterologous cell-specific binding site; and (b) a nucleic acid present in the protein envelope which comprises sequences for a virus-specific packaging signal and a structural gene.

The term "cell permeability-mediating peptide" includes any peptides capable of mediating a cell permeability for substances, in particular proteins. These are in particular the peptides indicated in the applicant's German patent application 198 50 718.6. Especially preferred is a peptide including the following amino-acid-(DNA)-sequence.

The term "cell-specific binding site" includes any binding sites of proteins and other small molecules via which the respective proteins or molecules can bind to cells. Examples of such binding sites are to be found in cytokines and growth factors. They are further to be found in ligands of hormone receptors, neurotransmitter receptors, blood cell surface receptors and integrin receptors. A preferred binding site is the α5β1-integrin binding site of fibronectin. In the following, this binding site is referred to as RGD and includes the amino arginine, glycine and aspartate.

The term "virus" includes DNA and RNA viruses, in particular adenoviruses, adeno-associated viruses, vaccinia viruses, baculoviruses, hepatitis C viruses, hepatitis A viruses, influenza viruses and hepadnaviruses. Examples of the latter are HBV, WHV ("woodchuck hepatitis virus"), GSHV ("ground squirrel hepatitis virus"), RBSHV ("red-bellied squirrel hepatitis virus") DHV ("Pekin duck hepatitis virus") and HHV ("heron hepatitis virus"), wherein HBV is preferred.

The term "virus protein" relates to any protein of a virus mentioned above which can be present in its entirety or partially in a fusion protein together with a cell permeability-mediating peptide and a heterologous cell-specific binding site in the form of a further peptide. The protein can also already contain the cell permeability-mediating peptide. An example of one such protein is LHBs. This protein is preferred, as are other surface proteins and core proteins, for example HBcAg. The term "heterologous" indicates that the protein does not intrinsically comprise the cell permeability-mediating peptide mentioned above. It can be advantageous when the homologous, i.e. intrinsically present binding site of the protein is switched off. It can be especially advantageous if the homologous binding site is replaced with the heterologous binding site.

The term "nucleic acid" includes RNA and DNA, wherein both can be single stranded and/or double stranded.

The term "virus specific packaging signal" indicates a signal sequence in the above nucleic acids, by means of which the nucleic acids are packaged into the protein envelope of a particle. The signal sequence is specific for an above-mentioned virus. A preferred signal sequence is that of HBV. This is to be found in the HBV DNA and is referred to in the literature as epsilon.

The term "structural gene" includes genes which code for polypeptides (proteins). Examples of such polypeptides are tumor necrosis factors, interferons, interleukins, lymphokines, growth factors, plasma proteins, for example clotting factors and metabolic enzymes, and receptors. In particular the polypeptides can be those which are capable of enhancing the immunogenicity of cells. These can be polypeptides lacking in tumor cells, for example cytokines such as IL-2 and GM-CSF, and co-stimulating molecules such as B7-1, tumor-associated antigens, for example NAGE1, tyrosinases and viral polypeptides, for example E7 from the human papilloma virus and EBNA-3 polypeptides from the Epstein-Barr virus. Furthermore, the polypeptides can be adapter polypeptides, oligomeriztion motifs of a polypeptide, polypeptide fragments of virus envelope polypeptides and hormones. The term "structural gene" further includes anti- SEQ ID NO:20  P  L  S  S  I  F  S  R  I  G  D  P
SEQ ID NO:21  CCC ATA TCG TCA ATC TTC TCG AGG ATT GGG GAC CCT sense oligonucleotides, peptide nucleic acids, consensus sequences for transcription factors and ribozymes.

According to the invention particles containing a fusion protein are preferred, wherein the fusion protein includes an LHBs or fragments thereof and a heterologous binding site, in particular RGD. It is advantageous if the heterologous binding site, for example RGD, is present in place of the homologous binding site. It is especially preferred if the fusion protein comprises the amino acid sequence of FIG. 1 or an amino acid sequence differing therefrom in one or more amino acids.

Furthermore, particles are preferred which contain a fusion protein which includes a HBcAG, a cell permeability-mediating peptide, for example as indicated in the German patent application 198 50 718.6, in particular with the amino acid sequence given above, and a heterologous binding site, in particular RGD. It is especially preferred if the fusion protein comprises the amino acid sequence of FIG. 2 or an amino acid sequence differing therefrom in one or more amino acids.

The term "an amino acid sequence differing in one or more amino acids" indicates that this amino acid sequence specifies a fusion protein which has comparable elements and functions as the fusion protein in FIG. 1 or FIG. 2 but which differs from the amino acid sequence of FIG. 1 or FIG. 2 up to 20%, preferably 10%.

A particle according to the invention can be prepared by conventional methods. If the particle contains for example a fusion protein including an LHBs in which the homologous binding site is replaced by a heterologous binding site, in particular RGD, a method containing the following method steps is advantageous: (a) cotransfection of cells containing a hepatitis B virus genome, wherein the cells do not express LHBs, with a first expression vector coding for a fusion protein including an LHBs, in which the homologous binding site is replaced by a heterologous binding site, in particular RGD, and with a second expression vector comprising a virus-specific packaging signal and a structural gene; and (b) isolation and purification of the particle.

If the particle contains a fusion protein including an HBcAg, a cell permeability-mediating peptide according to the German patent application 198 50 718.6, in particular the peptide with the above amino acid sequence, and a heterologous binding site, in particular RGD, then a method including the following steps is advantageous: (a) cotransfection of cells containing an HBV polymerase with a first expression vector coding for a fusion protein including HBcAg, a cell permeability-mediating peptide according to the German patent application 198 50 718.6, in particular the peptide with the above amino acid sequence, and a heterologous binding site, in particular RGD, and with a second expression vector comprising a virus-specific packaging signal and a structural gene; and (b) isolation and purification of the particle.

With respect to the terms "expression vector", "cells" and "isolation and purification", reference is made to the explanations below, in particular in the examples. The cells also represent subject matter of the present invention. With respect to the other terms, reference is made to the above explanations.

Further subject matter is a fusion protein including an HBcAg, a cell permeability-mediating peptide and heterologous binding site, in particular RGD. The fusion protein preferably includes the amino acid sequence of FIG. 2 or an amino acid sequence differing therefrom in one or more amino acids.

With respect to the term "an amino acid sequence differing in one or more amino acids", reference is made to the above explanations.

Further subject matter of the present invention is a nucleic acid coding for a fusion protein mentioned above. The nucleic acid can be an RNA or a DNA. Preferably it is a DNA which includes (a) the DNA of FIG. 2 or 2 or a DNA differing therefrom b one or more base pairs, (b) a DNA related to the DNA of (a) by virtue of the degenerate genetic code.

The term "a DNA differing by one or more base pairs" indicates that this DNA codes for a fusion protein which comprises comparable elements and functions as the fusion protein of FIG. 1 or 2, but which differs from the base sequence of FIG. 1 or 2 such that, in the amino acid sequence, a difference of maximum 20%, preferably 10% is present.

A DNA according to the invention can exist as such or in a vector. A DNA according to the invention can in particular exist in an expression vector. Examples of such expression vectors are known to one of ordinary skill in the art. In the case of an expression vector for *E. coli*, these are for example pGEMEX, pUC derivatives, pGEX-2T, pET3b and pQE-8. pY100 and Ycpad1 are examples for expression in yeast, while pKCR, pEFBOS, cDM8, pCEV4, pcDNA3, pKSV10, RCMB and pRK5 are examples for the expression in animal cells. The bacculo virus expression vector pAc-SGH is NT-A is especially suitable for expression in insect cells.

One of ordinary skill in the art knows suitable cells for the expression of the DNA according to the invention present in an expression vector. Examples of such cells include the *E. coli* strains HB101, DH1, x 1776, JM101, JM 109, BL21, SG 13009 and M15pRep4, the yeast strain *Saccharomyces cerevisiae*, the animal cells L, NIH 3T3, FM3A, CHO, COS, Vero, HeLa, Hep62, CCL13 and 293, the insect cells Sf9 and sf21 and the plant cells Lupinus albus.

One of the ordinary skill in the art knows methods and conditions for the transformation or transfection of cells with an expression vector containing the DNA according to the invention as well as for the cultivation of the cells. He also knows methods for the isolation and purification of the virus protein expressed by the DNA according to the invention.

Further subject matter of the present invention is an antibody directed against the fusion protein mentioned above. Such an antibody can be made by conventional methods. It can be polyclonal or monoclonal. In making it, it is advantageous to immunize animals, in particular rabbits or chickens for a polyclonal antibody and mice for a monoclonal antibody, with the fusion protein. Further "boosters" of the animals with the fusion protein can also take place. The polyclonal antibody can then be obtained from the serum or the egg yolk of the animals. For monoclonal antibodies, the spleen cells of the animals are fused with myeloma cells.

Further subject matter of the present invention is a kit. Such a kit includes one or more of the following components: (a) a fusion protein according to the invention; (b) a DNA according to the invention; (c) an antibody according to the invention; as well as (d) normal adjuvants such as carriers, buffers, solvents, controls, etc.

One or more representatives for each of the individual components can be present. With regard to the individual terms, reference is made to the above explanations.

The present invention provides a gene transfer system which is specific, in other words with which the desired cells can be reached and genes can be introduced into these cells. The cells can be present individually or in a tissue. Furthermore, the cells can be isolated or can be present in the body of an individual. The present invention is therefore suitable for an ex vivo or in vivo therapy of cells or tissues, respectively. The application of the present invention can be monitored and controlled by antibodies according to the invention.

The present invention therefore represents a major step forward as a way of performing directed modifications to cells or tissues by gene therapy.

BRIEF DESCRIPTION OF THE DRAWINGS

FIG. 1 shows the amino acid and DNA sequences of a fusion protein according to the invention which includes an LHBs and the heterologous binding site RGD, wherein the latter replaces the homologous site.

FIG. 2 shows the amino acid and DNA sequences of a fusion protein according to the invention which includes an HBcAg, a cell permeability-mediating peptide of the above amino acid sequence and the heterologous binding site RGD.

DESCRIPTI N OF THE INVENTION

The present invention is explained by way of the following examples.

EXAMPLE 1

Preparation of a Particle According to the Invention which Contains a Fusion Protein Including an LHBs and a Heterologous Binding Site (A) Preparation of an Expression Vector Coding for all HBV-Specific Proteins with the Exception of LHBS To achieve this, one starts from the plasmid pTKTHBV2 (cf. Will et al., Proc. Natl. Acad. Sci. 82 (1985), 891–895). This contains two copies of the HBV genome. A fragment from ntHBV2821 (first copy) to ntHBV2870 (second copy) is amplified in a first PCR. The forward primer (nt 2821-2855) comprises the following sequence: CCA TAT TCT TGG GAA CAA GAT ATC CAG CAC GGG GC (SEQ ID NO:5) An EcoRV cleavage site is underlined. The triplet ACG between nt 2849-2852 replaces the ATG start codon of LHBs. The backward primer (nt 2877-2845) comprises the following sequence: GGA TTG CTG GTG GAA GAT ATC TGC CCC GTG CTG (SEQ ID NO:6). An EcoRV cleavage site is underlined. The triplet CGT between nt 2852-2849 replaces the natural triplet. CAT. PCR fragments obtained are digested with EcoRV and are purified on a preparative 1% agarose gel. A fragment of about 3.3 kb in size is eluted from the gel and is stored. In a second PCR, a forward primer comprising an EcoRV cleavage site followed by the subsequent sequence ntHBV2860 (second copy)-2878 (first copy) (CAG CAC GGG GCA GAT ATC TTC CAC CAG CAA TCC (SEQ. ID NO:7), and a backward primer comprising an EcoRV cleavage site followed by the subsequent sequence ntHBV 2830-2810 (GC CCC GTG CTG GAT ATC ATC TTG TTC CCA AGA ATA TGG) (SEQ ID NO:8) are used. PCR fragments obtained are digested with EcoRV and are purified on a preparative 1% agarose gel. A fragment of the expected size is eluted from the gel and is dephosphorylated. This fragment is used in a ligase reaction with the above fragment of approximately 3.3 kb, wherein the HBV expression vector pTKTHBV2Ldef is obtained. This expression vector codes for all HBV-specific proteins with the exception of LHBs.

(B) Preparation of an Expression Vector which Codes F r A Fusion Protein Including an LHBS and the Heterologous Binding Site RGD The fragment ntHBV2990-834 is amplified by PCR starting from the plasmid pTKTHBV2 (cf. above). The 5' primer comprises the following sequence: AAA AGA TCT GGC CGT GGC GAA GGA GCT GGA GCA TTC (SEQ. ID NO:9). This sequence includes a BgIII cleavage site followed by an ATG start codon and the sequence coding for the tripeptide RGD. The PreS1-specific reading from is used. The 3' primer comprises the following sequence: AAA AGA TCT GGT TTA AAT GTA TAC CCA AAG (SEQ. ID NO:10). This sequence includes a BgIII cleavage site. PCR fragments obtained are digested with BgIII and are inserted in the vector pcDNA.3 (Invitrogen), which has been cleaved with BgHI and dephosphorylated, whereby the expression vector pCRGDLHBs is obtained. this expression vector codes for an N-terminally shortened LHBs including the RGD binding site.

(C) Preparation of an Expression Vector which Comprises a Structural Gene and a Packaging Signal A sequence coding for the HBV packaging signal epsilon, for example ntHBV 1840-1914, is amplified by PCR. An EcoRV cleavage site is introduced via the primer used. The sequence of the forward primer reads: CCC GAT ATC ATG TCA TCT CTT GTT CAT GTC CTA (SEQ ID NO:11). The sequence of the backward primer reads: GGG GAT ATC GGT CGA TGT CCA TGC CCC AAA (SEQ ID NO:12). PCR fragments obtained are cleaved with EcoRV and are inserted in the vector pcDNA.3 (cf. above) which has been cleaved with EcoRV and desphosphorylated, whereby the vector pcVPHBV is obtained. This vector contains the HGV-specific packaging signal epsilon.

Starting from the vector pCeGFP (Invitrogen) coding for a "green fluorescent protein" under the control of the CMV promoter, the sequence containing the CMV promoter and the GPF gene is amplified by PCR. The forward primer has the following sequence: GGG GGA TCC CGA TGT ACG GGC CAG ATA TAC GCG TTG (SEQ ID NO: 13). The backward primer has the following sequence: GGG GGA TCC GCG GCC GCT TTA CTT GTA (SEQ ID NO:14). The primers used each contain a BamHI cleavage site. PCR fragments obtained are cleaved with BamHI and are inserted into the vector pCVPHBV (Invitrogen) which has been cleaved with BamHI and dephosphorylated, whereby the expression vector pCVPHBVeGPF is obtained. This expression vector contains the HBV-specific packaging signal epsilon, the CMV promoter and a sequence coding for eGFP.

(D) Preparation of a Packaging Cell

Approximately $0.8 \times 10^6$ HepG2 cells are transfected with 4 µg of pTKTHBV2Ldef (cf. (A)) and 2 µg of pcDNA.3 (cf. (B)) by means of lipofection. pcDNA.3 codes for G418 resistance. 2 h after transfection, the cells are transferred into a medium containing 700 mg G418/l. G418-resistant clones are subcultured after 14d. The stable integration of pTKTHBV2Ldef is confirmed by means of PCR and southern blots. The expression of the surface protein SHBs from HBV and from HBcAg is confirmed by means of specific antibodies in ELISAS. The packaging cell line HepG2-TKTHBV2Ldef is obtained. This cell line expresses all HBV-specific proteins with the exception of LHBs.

(E) Preparation of Particles According to the Invention

Approximately $0.8 \times 10^6$ cells of the packaging cell line of (D) are transfected with 3 µg of pCRGLHBs (cf. (B)) and 3

µg of pCVPHBVeGFP (cf. (B)) by means of lipofection. 72 h after transfection, the cells or their supernatants, respectively, are collected and subjected to a PEG precipitation. Subsequently, a CsCI density gradient centrifugation is performed. The particles according to the invention are obtained in pure form. These particles include all HBV-specific proteins with the exception of LHBs, which is replaced by a RGD-LHBs.

EXAMPLE 2

Preparation of a Particle According to the Invention which Contains a fusion protein including an HBcAg, a Cell Permeability-Mediating Peptide and a Heterologous Binding Site A DNA coding for a cell permeability-mediating peptide (subsequently referred to as ZPP) is used. This DNA has the following sequence: XXX AGA TCT ATG CCC ATA TCG TCA ATC TTC TCG AGG ATT GGG GAC CCT GGA TCC XXX (X denotes any nucleotide) (SEQ ID NO:15). This sequence has its 5'-end a BglII cleavage site, followed by an ATG start codon and, at its 3'-end, a BamHI cleavage site. A double stranded DNA molecule based on the above sequence is cut with BamHI/BglII and is inserted into the expression vector pcDNA.3 (cf. above), which has been cleaved with BamHI and dephosphorylated, whereby the expression vector pCZPP is obtained.

Furthermore, the expression vector pTKTHBV2 (cf. above) is used to amplify the fragment nt-HBV 1861-2136 by means of PCR. The forward primer includes the following sequence: XXX GGA TCC ACT GTT CAA GCC TCC AAG CTG (SEQ ID NO:16). This sequence includes a BamHI cleavage site followed by the sequence ntHB 1861-1881. The backward Primer includes the following sequence: XXX GAA TTC TGG ATC TTC CAA ATT AAC ACC CAC CCA (SEQ ID NO:17). This sequence includes an EcoRI cleavage site followed by the sequence ntHBV 2139-2116. In a second PCR, the fragment ntHBV 2140-2480, which is extended at its 5'-end with the sequence coding for the RGD motif, is amplified. The forward primer includes the following sequence: XXX GAA TTC CGA GGC GAC GCG TCT AGA GAC CTA GTA GTC (SEQ ID NO:18). This sequence includes and EcoRI cleavage site followed by the sequence coding for the RGD motif, and the sequence ntHV2140-2161. The backward primer includes the following sequence: XXX AAG CTT TCC CCA CCT TAT GAG TCC AAG (SEQ ID NO:19). This sequence includes a HindIII-cleavage site and the sequence ntHBV 2480-2460.

Fragments obtained from both PCRs are cleaved with EcoRI and are ligated with one another. The litigation product is used as a template for a further PCR, wherein the forward primer from the first litigation product is used as a template for a further PCR, wherein the forward primer from the first PCR is used as a forward primer and the backward primer from the second PCR is used as a backward primer. PCR fragments obtained are cleaved with BamHI/HindIII and are inserted into the vector pCZPP, which has been cleaved with BamHI/HindIII and has been dephosphorylated, whereby the expression vector pCZPPHBcRGC is obtained. This expression vector codes for HBcAG containing the ZPP sequence at the N-terminus and the RGD sequence in the region of the amino acids 79–82.

Furthermore approximately $0.8 \times 10^6$ HepG2 cells are transfected by means of lipofection with 4 µg of an expression vector coding for HBV polymerase and with 2 µg pCDN3. Here, reference is made to the previous description from example 1 (D). A cell line denoted as HepG2-HBV Pol is obtained.

Approximately $0.8 \times 10^6$ cells of the cell line HepG2-HBV Pol are transfected with 3 µg of pCZPPHBc RGC and 3 µg of pCVPHBVeGPF (cf. example 1,B) by means of lipofection. Here, reference is made to the above description of example 1(E). Particles according to the invention are obtained in pure form.

EXAMPLE 3

Detection of the Expression of a Nucleic Acid Present in Particles According to the Invention in Fibroblasts Approximately $1 \times 10^9$ particles according to the invention form example 1(E) or example 2 are solubilized in 100 µl 0.9% saline and are injected into the tail vein of balb/c nice. The soleus-and the tibialis anterior muscle is isolated at 48 h after injection and is slowly frozen in a "tissue tag". Cryo-slices are prepared from the frozen preparation and are analyzed under a fluorescence microscope with blue excitation.

A green fluorescence in the fibroblasts is obtained, indicating the expression of the "green fluorescent protein".

EXAMPLE 4

Preparation and Purification of a Fusion Protein According to the Invention

The fusion protein of FIG. 1 according to the invention is made. To this end, DNA from FIG. 1 is provided at the 5'-end with a BglII linker and at the 3'-end with a BglII linker and is subsequently cleaved with the corresponding restriction enzymes. The BglII/BglII fragment obtained is inserted into the expression vector pQE8 cleaved with BamHI, so that the expression plasmide pQE8/LHBs is obtained. Such a plasmid codes for a fusion protein made of 6 histidine residues (N-terminus partner) and the fusion protein according to the invention from FIG. 1 (C-terminus partner). pQE8/LHBs is used for the transformation of E. coli SG 13009 (cf. Gottesman, S. et. al., J. Bacteriol. 148, (1981), 265–273). The bacteria are cultivated in an LB medium with 100 µg/ml ampicillin and 25 µg/ml kanamycin and are induced for 4 h with 60 µM Isopropyl-B-D-Thiogalactopyranoside (IPTG). Lysis of the bacteria is achieved by addition of 6 M guanidine hydrochloride, whereafter chromatography (Ni-NTA-Resin) of the lysate is performed in the presence of 8 M urea according to the directions of the manufacturer (Qiagen) of the chromatography material. The bound fusion protein is eluted in a buffer at pH 3.5. Following neutralization, the fusion protein is subjected to 18% SDS polyacrylamide gel electrophoresis and is stained with coomassie blue (cf. Thomas, J. O. and Kornberg, R. D., J. Mol. Biol. 149 (1975), 709–733).

It has been found that a fusion protein according to the invention can be made in highly pure form.

EXAMPLE 5

Preparation and Detection of an Antibody According to the Invention

A fusion protein of example 4 according to the invention is subjected to 18% SDS polyacrylamide gel electrophoresis. After staining of the gel with 4 M sodium acetate, a 38 kD band is cut out of the gel and is incubated in phosphate-buffered saline solution. Pieces of the gel are sedimented prior to determination of the protein concentration of the supernatant by SDS polyacrylamide gel electrophoresis and staining with coomassie blue. Animals are immunized with the gel-purified fusion protein as follows:

A) Immunization Protocol for Polyclonal Antibodies in Rabbits

35 μg of gel-purified fusion protein in 0.7 ml PBS and 0.7 ml complete or incomplete Freund's adjuvant are used for each immunization.

Day 0: 1. Immunization (complete Freund's adjuvant)
Day 14: 2. Immunization (incomplete Freund's adjuvant; icFA)
Day 28: 3. Immunization (icFA)
Day 56: 4. Immunization (icFA)
Day 80: bleeding The rabbit serum is tested in an immunoblot. To this end, a fusion protein from example 4 according to the invention is subjected to SDS polyacrylamide gel electrophoresis and is transferred to a nitrocellulose filter (cf. Khyse-Andersen, J., J. Biochem. Biophys. Meth. 10, (1984), 203–209). Western blot analysis as described in Bock, C.-T. et al., Virus Genes 8, (1994), 215–229 was performed. To this end, the nitrocellulose filter is incubated for 1 h at 37° C. with a first antibody. This antibody is the serum of the rabbit (1:10000 in PBS). After multiple wash steps with PBS, the nitrocellulose filter is incubated with a second antibody. This antibody is a monoclonal goat anti-rabbit IgG antibody (Dianova) coupled with alkaline phosphatase (1:5000) in PBS. After 30 minutes of incubation at 37° C., multiple wash steps with PBS follow and subsequently the alkaline phosphatase detection reaction is performed with development solution (36 μM 5' bromo-4-chloro-3-indolylphosphate, 400 μM nitroblue tetrazolium, 100 mM Tris-HCl, pH 9.5, 100 mM NaCl, 5 mM $MgCl_2$) at room temperature until bands become visible.

It has been found that polyclonal antibodies according to the invention can be prepared.

B) Immunization Protocol for Polyclonal Antibodies in Chicken

40 μg of gel-purified fusion protein in 0.8 ml PBS and 0.8 ml complete or incomplete Freund's adjuvant are used for each immunization.

Day 0: 1. Immunization (complete Freund's adjuvant)
Day 28: 2. Immunization (incomplete Freund's adjuvant; icFA)
Day 50: 3. Immunization (icFA)

Antibodies are extracted from egg yolk and are tested by western blot. Polyclonal antibodies according to the invention are detected.

C) Immunization Protocol for Monoclonal Antibodies of Mice

12 μg of gel-purified fusion protein in 0.25 ml PBS and 0.25 ml complete or incomplete Freund's adjuvant are used for each immunization; In the fourth immunization, the fusion protein is solubilized in 0.5 ml (without adjuvant).

Day 0: 1. Immunization (complete Freund's adjuvant)
Day 28: 2. Immunization (incomplete Freund's adjuvant; icFA)
Day 56: 3. Immunization (icFA)
Day 84: 4. Immunization (PBS) Day 87: fusion Supernatants from hybridomas are tested by Western blot. Monoclonal antibodies according to the invention are detected.

What is claimed is:

1. A particle comprising:

(a) a protein envelope with a fusion protein, the fusion protein comprising a virus protein, a cell permeability-mediating peptide, and a heterologous cell-specific binding site; and (b) nucleic acid sequences present within the protein envelope, each of the nucleic acid sequences comprising a sequence encoding a virus-specific packaging signal and a sequence encoding a structural gene, wherein the cell permeability-mediating peptide comprises the amino acid sequence set forth in SEQ ID NO:20.

2. The particle of claim 1, wherein the virus protein is from a virus selected from the group consisting of adenovirus, adeno-associated virus, vaccinia virus, baculovirus and hepadnavirus.

3. The particle of claim 2, wherein the hepadnavirus is a hepatitis B virus.

4. The particle of claim 1, wherein the virus protein is a surface protein.

5. The particle of claim 1, wherein the virus protein is a core protein.

6. The particle of claim 5, wherein the core protein is an HBcAg.

7. The particle of claim 1, wherein the heterologous cell-specific binding site is RGD.

8. A particle comprising:

(a) a protein envelope with a fusion protein, the fusion protein comprising a virus protein, a cell permeability-mediating peptide, and a heterologous cell-specific binding site; and (b) nucleic acid sequences present within the protein envelope, each of the nucleic acid sequences comprising a sequence encoding a virus-specific packaging signal and a sequence encoding a structural gene, wherein the fusion protein consists of the amino acid sequence set forth in SEQ ID NO:1.

9. The particle of claim 1, wherein the fusion protein comprises the amino acid sequence set forth in SEQ ID NO:2.

10. A particle comprising:

(a) a protein envelope with a fusion protein, the fusion protein comprising a virus protein, a cell permeability-mediating peptide, and a heterologous cell-specific binding site; and (b) nucleic acid sequences present within the protein envelope, each of the nucleic acid sequences comprising a sequence encoding a virus-specific packaging signal and a sequence encoding a structural gene, wherein the fusion protein consists of the amino acid sequence set forth in SEQ ID NO:2.

* * * * *